(12) United States Patent
High et al.

(10) Patent No.: US 7,022,484 B2
(45) Date of Patent: Apr. 4, 2006

(54) METHODS FOR TREATING NEUROPATHOLOGICAL STATES AND NEUROGENIC INFLAMMATORY STATES AND METHODS FOR IDENTIFYING COMPOUNDS USEFUL THEREIN

(75) Inventors: Karin Westlund High, League City, TX (US); Giulio Taglialatela, Dickinson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 665 days.

(21) Appl. No.: 09/877,220

(22) Filed: Jun. 8, 2001

(65) Prior Publication Data

US 2002/0028779 A1   Mar. 7, 2002

Related U.S. Application Data

(60) Provisional application No. 60/225,702, filed on Aug. 16, 2000, provisional application No. 60/210,413, filed on Jun. 8, 2000.

(51) Int. Cl.
*G01N 33/567* (2006.01)
*A61K 39/395* (2006.01)
*C07K 1/00* (2006.01)

(52) U.S. Cl. .................. 435/7.1; 435/7.21; 435/7.8; 424/9.1; 424/130.1; 424/143.1; 436/501; 530/350; 530/388.22; 514/2; 514/27

(58) Field of Classification Search ................ 436/501; 435/7.1, 7.21; 530/350, 388.22; 514/2, 514/27
See application file for complete search history.

(56) References Cited

OTHER PUBLICATIONS

Rao et al., Neuron, 19(801-812)1997.*
Marsh et al., J. Neurochemistry 77(23-33)2001.*
Hall and Soderling, J. Biol. Chem. 272(4135-4140)1997.*
Ehlers, et al., J. Neuroscience 18(2)720-730, 1998.*
Skeberdis, et al., PNAS 98(6)3561-3566, 2001.*
Wang, YT et al., PNAS 93(1721-1725)1996.*
Ehlers, MD et al., Science 269(1734-1737)1995.*
Abe et al., "Tyrosine kinase inhibitors, herbimycin A and lavendustin A, block formation of long-term potentiation in the dentate gyrus in vivo," Brain Res. Sep. 3, 1993;621(1): 167-170.

Akaike et al., "Regulation by neuroprotective factors of NMDA receptor mediated nitric oxide synthesis in the brain and retina," Prog Brain Res. 1994;103:391-403.
Akiyama et al., "Genistein, a specific inhibitor of tyrosine-specific protein kinases," J Biol Chem. 1987 Apr. 25;262 (12):5592-5.
American Type Culture Collection, "ATCC No. CRL-1721," organism:*Rattus norvegicus*; designation: PC-12; tissue: pheochromocytoma [online]. Manassas; VA [retrieved on Jan. 30, 2002]from the Internet. Retrieved from the Internet URL: <http://phage.atcc.org/cgi-bin/searchengine/longview.cgi?view=ce,921526,CRL-1721&text=crl-1721>; 3 pages.
American Type Culture Collection, "ATCC No. CRL-2266," organism: *Homo sapiens*; designation: SH-SY5Y; tissue: neuroblastoma [online]. Manassas, VA [retrieved on Jan. 30, 2002] from the Internet. Retrieved from the Internet URL: <http://phage.atcc.org/cgi-bin/searchengine/longview.cgi?view=ce,1751936,CRL-2266&text=crl-2266>; 3 pages.
American Type Culture Collection, "ATCC No. HTB-93," organism: *Homo sapiens*; designation: SW 982; tissue: synovial sarcoma [online]. Manassas, VA [retrieved on Jan. 30, 2002] from the Internet. Retrieved from the Internet URL: <http://phage.atcc.org/cgi-bin/searchengine/longview.cgi?view=ce,4882733,HTB-93&text=htb-93>; 3 pages.
Benes et al., "Rapid activation and nuclear translocation of mitogen-activated protein kinases in response to physiological concentration of glucose in the MIN6 pancreatic β cell line," J Biol Chem. 1998 Jun. 19;273(25): 15507-13.
Boulikas, "Nuclear import of protein kinases and cyclins," J Cell Biochem. Jan. 1996;60(1):61-82.
Coderre, "Examination of the evidence that distinct excitatory amino acid receptors and intracellular messengers mediate thermal and mechanical hyperalgesia," American Pain Society J. 1994;3(4):232-9.

(Continued)

*Primary Examiner*—Elizabeth Kemmerer
*Assistant Examiner*—Michael Brannock
(74) *Attorney, Agent, or Firm*—Mueting, Raasch & Gebhardt, P.A.

(57) ABSTRACT

The present invention provides methods for treating neuropathological states and neurogenic inflammatory states in a subject. The present invention also provides methods for identifying compounds that can be used to treat such states. Preferably, the compounds alter the distribution of NMDA glutamate receptor NR1 subunit in cells, and/or alter the production of TNFα by cells.

28 Claims, 3 Drawing Sheets

OTHER PUBLICATIONS

Dougherty et al., "Hyperalgesia and amino acids—Receptor selectivity based on stimulus intensity and a role of peptides," *Amer Pain Soc J.* 1994;3(4):240-8.

Duarte et al., "Effect of tyrosine kinase and tyrosine phosphatase inhibitors on aortic contraction and induction of nitric oxide synthase," *Eur J Pharmacol.* Oct 29, 1997;338(1):25-33.

Fadool et al., "Tyrosine phosphorylation modulates current amplitude and kinetics of a neuronal voltage-gated potassium channel," *J Neurophysiol.* Sep. 1997;78(3):1563-1573.

Guerrini et al., "Glutamate-dependent activation of NF-κB during mouse cerebellum development," *J Neurosci.* Aug. 15, 1997;17(16):6057-63.

Hargreaves et al., "A new and sensitive method for measuring thermal nociception in cutaneous hyperalgesia," *Pain.* Jan. 1988;32(1):77-88.

Heilmeyer, ed., *Signal Transduction and Protein Phosphorylation*, Proceedings of a NATO/FEBS Summer School on Signal Transduction and Protein Phosphorylation, held Sep. 14-26, 1996 at Korgialenios School, Island of Spetsai, Greece; Plenum Press, New York, NY; 1987; title page, publisher's page and table of contents only: 6 pages.

Kaufmann et al., "Oxidative-stress-dependent up-regulation of Bcl-2 expression in the central nervous system of aged Fisher-344 rats," *J Neurochem.* Feb. 2001; 76(4):1099-108.

Liu et al., "Evidence for presynaptic N-methyl-D-aspartate autoreceptors in the spinal cord dorsal horn," *Proc Natl Acad Sci U S A.* Aug. 30, 1994;91(18):8383-7.

Lu et al., "Tyrosine kinase inhibitor, genistein, reduces spinal NMDA receptor expression increases in carrageenan-induced acute arthritis model," [online]. Abstract of poster presented at American Pain Society 18th Annual Scientific Meeting, Oct. 21-24, 1999 Fort Lauderdale, FL; [retrieved on Jan. 30, 2002]. Retrieved from Internet:<URL:http://www.ampainsoc.org/abstract/1999/data/115/index.html>; 1 page.

Lu et al., "Tyrosine kinase inhibitor, genistein, reduces spinal NMDA receptor expression increases in carrageenan-induced acute arthritis model, " *Abstracts.* 1999;25:920 (Abstract 371.2); presented at Society for Neuroscience Annual Meeting in Miami Beach, FL; Oct. 23-28, 1999 (1 page).

Lu et al., "Src activation in the induction of long-term potentiation in CA1 hippocampal neurons," *Science.* Feb. 27, 1998:279(5355): 1363-7.

Millan, "The induction of pain: and integrative review," *Prog Neurobiol.* Jan. 1999;57(1): 1-164.

Neugebauer et al., "Peripheral and spinal components of the sensitization of spinal neurons during an acute experimental arthritis," *Agents Actions.* Dec. 1998;25(3-4):234-6.

O'Byrne et al., "Elevated substance P and accelerated cartilage degradation in rabbit knees injected with interleukin-1 and tumor necrosis factor," *Arthritis Rheum.* Jul. 1990;33(7): 1023-8.

Ohmichi et al., "Inhibition of the cellular actions of nerve growth factor by staurosporine and K252A results from the attenuation of the activity of the *trk* tyrosine kinase" *Biochemistry.* Apr. 28, 1992;31(16):4034-9.

Panté et al., "Toward the molecular dissection of protein import into nuclei," *Curr Opin Cell Biol.* Jun. 1996;8(3): 397-406.

Planells-Cases et al., "Molecular cloning, functional expression, and pharmacological characterization of an *N*-methyl-D-aspartate receptor submit from human brain," *Proc Natl Acad Sci U S A.* Jun. 1, 1993;90(11):5057-61.

Ritchlin, "Fibroblast biology. Effector signals released by the synovial fibroblast in arthritis," *Arthritis Res.* 2000;2(5): 356-60.

Schulman, "Signal transduction and protein phosphorylation," Chapter 4 in *The Cortical Neuron*, Gutnick et al., eds.; Oxford University Press, New York, NY; pp. 52-65 (1995).

Siebenlist et al., "Structure, regulation and function of NF-κB," *Annu Rev Cell Biol.* 1994;10:405-55.

Skilling et al., "Extracellular amino acid concentrations in the dorsal spinal cord of freely moving rats following veratridine and nociceptive stimulation," *J Neurochem*, Jul. 1998;51(1):127-32.

Sluka et al., "An experimental arthritis in rats: dorsal horn aspartate and glutamate increases," *Neurosci Lett.* Oct. 12, 1992;145(2):141-4.

Sluka et al., "Reduction in joint swelling and hyperalgesia following post-treatment with a non-NMDA glutamate receptor antagonist," *Pain.* Oct. 1994;59(1):95-100.

Sorkin et al., "Microdialysis recovery of serotonin released in spinal cord dorsal horn," *J Neurosci Methods.* Mar. 1988;23(2):131-8.

Takizawa et al., "Use of 1.4-nm immunogold particles for immunocytochemistry on ultra-thin cryosections," *J Histochem Cytochem.* Dec. 1994;42(12):1615-23.

Wang et al., "Regulation of NMDA receptors by tyrosine kinases and phosphatases," *Nature.* May 19, 1994;369 (6477):233-5.

Weis, "Importins and exportins: how to get in and out of the nucleus," *Trends Biochen Sci.* May 1998;23(5):185-9.

Westlund et al., "Nuclear translocation of NMDA R1-like immunoreactivity and other increases after knee joint inflammation," *Abstracts.* 1999;25:920(Abstract 371.1); presented at Society for Neuroscience Annual Meeting in Miami Beach, FL; Oct. 23-29, 1999 (1 page).

Westland-High, "Central control of arthritis and arthritic pain," Grant Abstract, Grant No. 5R01NS032778-04 [online]. National Institute of Neurological Disorders and Stroke, National Institutes of Health, Bethesda, MD; project dates Feb. 1, 1995 to Jan. 31, 2001 [retrieved on Jan. 30, 2002]. Retrieved from the Internet: <URL:http://commons.cit.nih.gov/crisp3/CRISP_LIB.getdoc?textkey=2655483& p_grant_num= 5R01NS032778-04&p_query=&ticket= 627812&p_audit_session_id=3757764&p_keywords=>; 2 pages.

Westland-High, "Neurogenic contributions to chronic arthritis," Grant Abstract, Grant No. 2P01NS011255-27A10039 [online]. National Institute of Neurological Disorders and Stroke, National Institutes of Health, Bethesda, MD; project dates Feb. 1, 1974 to Jul. 31, 2006 [retrieved on Jan. 30, 2002]. Retrieved from the Internet: <URL:http://commons.cit.nih.gov/crisp3/CRISP_LIB. getdoc?textkey=6545920&p_grant_num=2P01NS011255-27A10039&p_query=&ticket=627846&p_audit_ session_id=3757764&p_keywords=>; 2 pages.

Yu et al., "NMDA channel regulation by channel-associated protein tyrosine kinase Src," *Science.* Jan. 31, 1997;275 (5300):674-8.

Zhang et al., "BCL3 encodes a nuclear protein which can alter the subcellular location of NF-κB proteins," *Mol Cell Biol.* Jun. 1994;14(6):3915-26.

\* cited by examiner

METHODS FOR TREATING NEUROPATHOLOGICAL STATES AND NEUROGENIC INFLAMMATORY STATES AND METHODS FOR IDENTIFYING COMPOUNDS USEFUL THEREIN

CONTINUING APPLICATION DATA

This application claims the benefit of U.S. Provisional Application Ser. No. 60/210,413, filed Jun. 8, 2000, and U.S. Provisional Application Ser. No. 60/225,702, filed Aug. 16, 2000, which are incorporated by reference herein.

GOVERNMENT FUNDING

The present invention was made with government support under Grant No. NS32778 and NS11255, awarded by the National Institutes of Health. The Government has certain rights in this invention.

BACKGROUND

Glutamate is the primary transmitter of most neurons in the nervous system, including those involved in sensing pain. Glutamate is typically locked up in nerve endings and is released in very small amounts at nerve junctions to signal when a nerve is activated. Glutamate attaches itself to specific receptive docking sites on the next nerve in sequence. In the case of ionotropic glutamate receptors the docking process allows a tiny channel to open, and a charge is transferred by sodium and calcium ions as a tiny electrical current. In the case of pain, the chemical message is converted to electrical energy and carried by the pain transmission nerves to specific sites in the nervous system that interpret the signals as pain. Typically, the precision of the nervous system depends on this event taking place in microseconds. The glutamate receptor site then closes rapidly, resetting for the next neuronal event.

Glutamate is released by neurons in high concentrations in each case of persistent pain and neural injury. In cases of severe pain, inflammation, and tissue damage, such as with arthritis, spinal cord injury or head injury, large amounts of glutamate escape and can be destructive. The damage that occurs in the presence of high glutamate concentrations translates into long-lasting pathological levels of pain and nervous tissue damage. These events also involve many other neuronal and inflammatory agents, but excess glutamate is an initiator in these long-term events that enhances the pain signal. In addition to prolonged pain, excessive glutamate for extended periods of time, as in severe injury, will poison and kill nerve cells. This is evident in cases of head injury and spinal cord damage where the secondary destruction by the presence of excess glutamate amplifies the initial damage caused by the event itself.

Nerve activation under normal conditions involves a glutamate receptor, non-NMDA ionotropic glutamate receptor, allowing sodium to enter the cell to activate the cell. Another glutamate receptor, NMDA ionotropic glutamate receptor, is a channel on the cell membrane allowing passage of calcium ions that carries a stronger electrical signal in normal transmission. This particular glutamate receptor, the NMDA glutamate receptor, is composed of two sets of two protein molecules, the NR1 and NR2 NMDA glutamate receptor subunits. They bind tightly to one another to form the ring through which the calcium signal is carried. A fifth subunit protein may sometimes accompany the four functional subunits.

In the case of persistent pain, the continual presence of glutamate will initiate a cascade of additional events beyond simple nervous event signaling. In addition to activation of both ion channel type glutamate receptors, other types of glutamate receptor complexes are activated called metabotropic receptor proteins. These are receptor proteins that when also activated have longer-lasting effects, sit adjacent to the NMDA glutamate receptor and can release stores of calcium inside the cell. Cascades of intracellular processes are then initiated. Most importantly, these cascades are capable of influencing the entire behavior of the nerve cell in a longer-lasting way if they signal and direct the future activities of the cell long-term by communicating with the cell nucleus.

Memory and learning function are closely related to persistent pain mechanisms. Memory and learning involve both types of ion transporting glutamate receptors, the ionotropic glutamate receptors, in the hippocampus and cortex of the brain. The cells in the hippocampus are activated by glutamate as the signal relaying transmitter. If the activation of this brain region is strong enough and persistent enough, then both ionotropic glutamate receptor types are activated to achieve a long-term memory of the event through a new "hard-wired" cortical neuronal circuit. This is similar to the "hard-wired" memory of the painful event that becomes a persistent process in the pain transmission circuitry, referred to as sensitization on the cellular level and persistent central pain state on the whole animal level. Further activation of the event to the point of becoming pathological amounts of chronic pain occurs by activation of other neuronal receptors, preferably in this case the metabotropic glutamate receptor producing long-term nuclear and cellular changes including the release of intracellular calcium and regulation of many enzymes (especially kinases and phosphatases). The cells are then overactivated and a sensitized, neuropathological state develops. In the neuropathological state the pain message is enhanced and may remain this way for a prolonged period of time.

The aim of basic science research in the field of pain is to provide better treatment for the millions of people who suffer from persistent pain. Current methods for pain control mainly use traditional pharmacological approaches in which small molecules are taken orally. Many of these medicines treat some of the symptoms of pain by attaching themselves to receptor molecules on the cell surface, including the glutamate receptor, in an attempt to compete with the nerves own transmitter chemicals. Currently, little is known about the processes that have already occurred within the cell that are already initiated after neuropathological neural signaling events have occurred and by which the high degree of persistent pain continues. A better understanding of these events would allow for more effective pain control.

SUMMARY OF THE INVENTION

This invention represents a significant advance in the art of identifying agents that can be used for the treatment of certain conditions, including neuropathological states and neurogenic inflammatory states.

The present invention provides a method for treating a neuropathological state in a subject. The method includes administering to the subject an effective amount of a tyrosine kinase inhibitor. The neuropathological state may be, for instance, persistent pain, arthritis, ulcerative colitis, inflammatory bowel disease, Crohn's disease, pancreatitis, asthma, stroke, brain injury, spinal cord injury, epileptogenesis, or viral invasion. The tyrosine kinase inhibitor may be, for instance, Genistein, Lavendustin A, K252a, or combinations thereof.

In another aspect, a method for treating a neuropathological state in a subject includes administering to the subject an effective amount of a compound that decreases the amount of NR1 subunit associated with a nucleus of a cell of the subject wherein the cell contains an NMDA glutamate receptor. The cell may be a neuron. Optionally, the neuron is a sensitized neuron or is prevented from being converted to a sensitized neuron. The compound may be a tyrosine kinase inhibitor such as Genistein, Lavendustin A, K252a, or combinations thereof.

In a further aspect, a method for treating a neuropathological state in a subject includes administering to the subject an effective amount of a compound that decreases the amount of Tumor Necrosis Factor alpha (TNFα) produced by a cell of the subject. The cell may be a synovial cell. The cell may optionally include an NMDA glutamate receptor. The compound may be a tyrosine kinase inhibitor such as Genistein, Lavendustin A, K252a, or combinations thereof.

The present invention also provides a method for identifying a compound that alters NR1 subunit distribution in a cell. The method includes contacting a cell with an effective amount of the compound, activating an NMDA glutamate receptor present on the cell, and detecting the distribution of NR1 subunit in the cell wherein detection of an alteration in the distribution of NR1 subunit in the cell contacted with the compound relative to the distribution of NR1 subunit in a cell not contacted with the compound indicates an alteration in the distribution of NR1 subunit. The cell may be a neuron. The compound may be a tyrosine kinase inhibitor.

The present invention provides a method for identifying a compound that alters the production of TNFα by a cell. The method includes contacting a cell with an effective amount of the compound, activating an NMDA glutamate receptor present on the cell, and detecting the amount of TNFα produced by the cell wherein detection of an alteration in the amount of TNFα produced by the cell contacted with the compound relative to the amount of TNFα produced by a cell not contacted with the compound indicates an alteration in the amount of TNFα produced by the cell. The cell may be a synovial cell.

The present invention provides a method for treating a neurogenic inflammatory state in a subject. The method includes administering to the subject an effective amount of a compound that decreases the amount of TNFα produced by a cell of the subject wherein the cell contains an NMDA glutamate receptor. The compound may be a tyrosine kinase inhibitor.

The present invention provides a method for treating arthritis in a subject. The method includes administering to the subject an effective amount of a compound that decreases the amount of TNFα produced by a synovial cell of the subject. The compound may be a tyrosine kinase inhibitor.

The present invention provides a method for altering NR1 subunit distribution in a cell. The method includes contacting a cell with an effective amount of the compound, activating an NMDA glutamate receptor present in the cell, and detecting the distribution of NR1 subunit in the cell wherein detection of an alteration in the distribution of NR1 subunit in the cell contacted with the compound relative to the distribution of NR1 subunit in a cell not contacted with compound indicates an alteration in the distribution of NR1 subunit. The NR1 subunit associated with a nucleus of a cell of the subject may be increased or decreased.

Definitions

As used herein, the terms "neuropathological state" and "neuropathological condition" are used interchangeably and refer to functional disturbances and/or pathologic changes in a subject's nervous system. Examples of functional disturbances include persistent pain, an inflammatory state, brain injury, spinal cord injury, epileptogenesis, and viral invasion. Examples of pathological changes include the presence of persistent pain due to functional disturbances and a decrease in mental function due to epileptogenesis, memory disturbances, and aging.

As used herein, "neurogenic inflammatory state" refers to conditions where high concentrations of a glutamate receptor agonist are present (for instance, released by a neuron) and interact with a glutamate receptor, preferably an NMDA glutamate receptor, that is present on a cell. The interaction of the agonist with the glutamate receptor results in the production of cytokines, preferably, tumor necrosis factor α (TNFα) by the cell. Types of neurogenic inflammatory states include, for instance, arthritis, ulcerative colitis, inflammatory bowel disease, Crohn's disease, pancreatitis, asthma, stroke, brain injury, and viral invasion.

As used herein, an "effective amount" is an amount effective to decrease or prevent in a subject the symptoms associated with a condition described herein.

As used herein, the term "glutamate receptor" refers to a receptor present on the outer cellular membrane of a cell that binds glutamate, glutamate agonists, or glutamate antagonists. There are two types of glutamate receptors, ionotropic and metabotropic. Binding of agonist, for instance glutamate, N-methyl-D-aspartate, aspartate (NMDA), glycine, serine, by an ionotropic glutamate receptor results in channel opening and the subsequent flow of ions through the channel. Binding of agonist, for instance glutamate, (1S, 3R)-1-aminocyclopentane-1,3-dicarboxylic acid (ACPD), quisqualic acid or ibotenic acid by a metabotropic glutamate receptor results in phosphoinositide hydrolysis and intracellular calcium mobilization. "Activation" of a transmitter-gated channel, for instance a glutamate receptor, refers to the opening of the channel or initiation of transmitter related events. Preferably, the glutamate receptor is an NMDA glutamate receptor.

As used herein, a "tyrosine kinase inhibitor" is a compound that inhibits the activity of a tyrosine kinase to catalyze the transfer of a phosphate group, typically the terminal phosphate group from an adenosine triphosphate (ATP) molecule, to a tyrosine residue present in a target protein. A tyrosine kinase inhibitor can act on receptors having intrinsic tyrosine kinase activity (receptor tyrosine kinases) and tyrosine kinases that are not associated with a receptor (non-receptor protein tyrosine kinases). Preferably, a tyrosine kinase inhibitor acts on a non-receptor protein tyrosine kinase.

As used herein, unless otherwise noted, the terms "translocate" and "translocation" refer to movement of the NR1 subunit from the cell membrane to the nuclear membrane, preferably the inner nuclear membrane.

As used herein, the term "neuron" refers to a conducting cell of the nervous system. A neuron releases a neurotransmitter, preferably glutamate, that binds a transmitter-gated channel, preferably a glutamate receptor, located on the cell surface of a cell. The cell having the glutamate receptor, preferably an NMDA glutamate receptor, may be a neuron or other cells as described herein.

As used herein, the term "subject" includes humans, as well as other animals (for instance, mice, rats, or rabbits) that can be used as animal models in the study of the conditions described herein.

As used herein, the term "NR1 subunit" refers to the NMDA glutamate receptor NR1 subunit.

As used herein, the term "sensitized neuron" refers to a neuron that has been altered such that activation of the neuron results in a response that is greatly enhanced relative to a non-sensitized neuron. Sensitized neurons play a role in allodynia or hyperalgesia. As used herein, the term "allodynia" refers to an increased sensitivity to a stimulus that was previously innocuous. For instance, a stimulus that was previously innocuous is now considered painful, i.e., noxious. As used herein, the term "hyperalgesia" refers to an increased sensitivity to a noxious stimulus. Allodynia and hyperalgesia can be primary or secondary. Primary allodynia and primary hyperalgesia mean the location of the increased sensitivity is at the same site as an injury. Secondary allodynia and secondary hyperalgesia mean the location of the increased sensitivity is at a site that is not identical as the site of the injury. A sensitized neuron typically has higher amounts of protein kinase C and nitric oxide (NO) synthase than neurons that are not sensitized.

As used herein, the term "persistent pain" refers to pain that continues for at least about 10 minutes after the initial stimulus causing the pain. Chronic pain is pain that lasts at least 3 weeks. Persistent pain includes chronic pain and any type of pain that lasts at least about 10 minutes.

Unless otherwise specified, "a," "an," "the," and "at least one" are used interchangeably and mean one or more than one.

DETAILED DESCRIPTION OF PREFERRED EMBODIMENTS OF THE INVENTION

Figure 1:
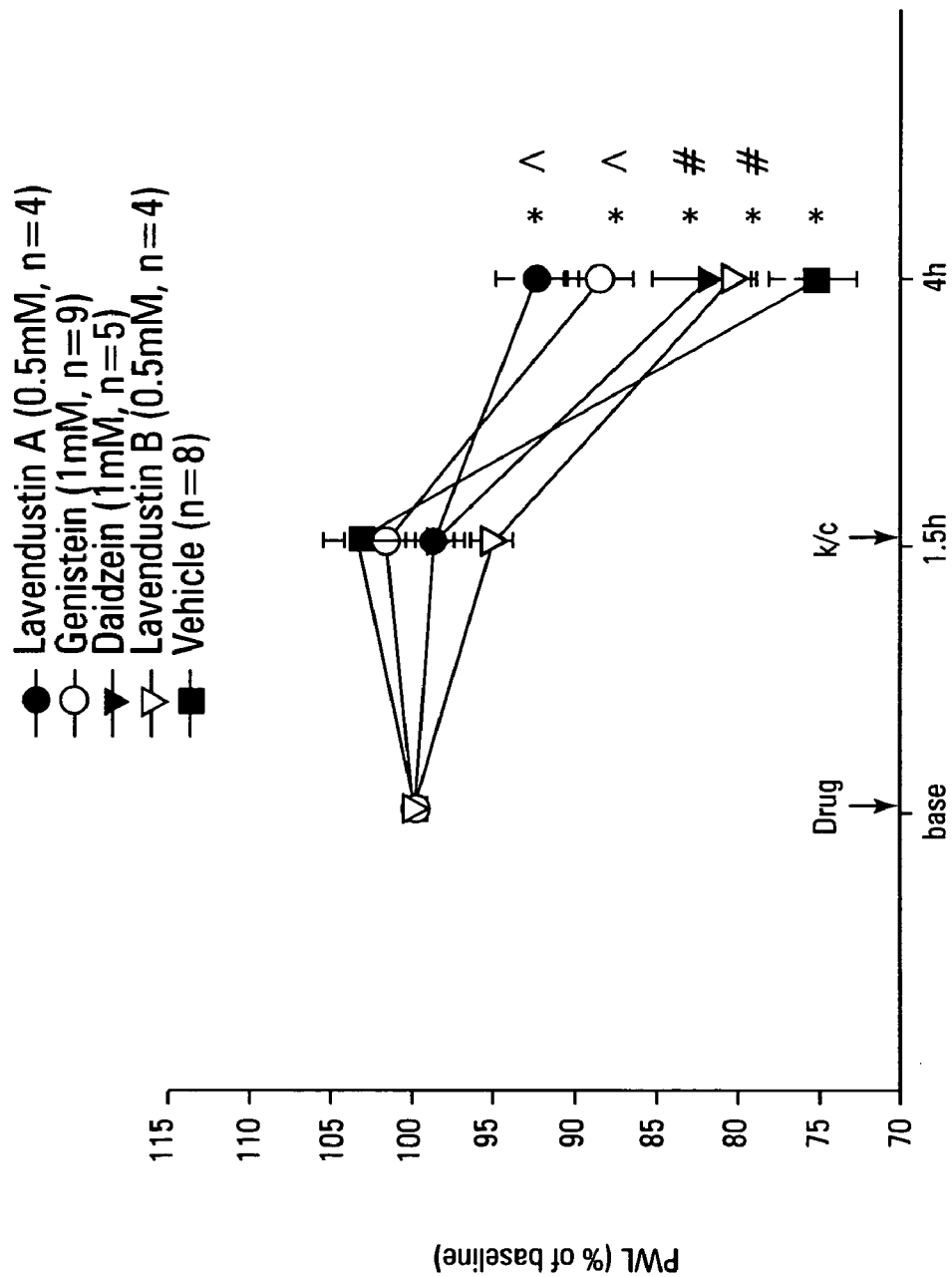
FIG. 1. Paw withdrawal latency (PWL) versus time. Base, beginning of experiment; 1.5 h, 1.5 hours; 4 h, 4 hours; drug, time at which Lavendustin A, Genistein, Daidzein, Lavendustin B, or vehicle was administered as described herein; k/c, time at which kaolin/carrageenan was administered as described herein to produce the experimental arthritis; *, one way Analysis of Variance (ANOVA) repeated measurement, planned comparison, $p<0.01$ versus baseline; #, one way ANOVA between-groups, planned comparison, $p<0.05$ (versus 4 hour Lavendustin A group); ^, one way ANOVA between-groups, planned comparison, $p<0.01$ (versus 4 hour vehicle A group).

The present invention provides methods for identifying compounds that alter the distribution of NR1 subunits and/or alter the production of Tumor Necrosis Factor Alpha (TNFα) in a cell. The cell can be ex vivo or in vivo. As used herein, the term "ex vivo" refers to a cell that has been removed from the body of a subject. Ex vivo cells include, for instance, primary cells (e.g., cells that have recently been removed from a subject and are capable of limited growth in tissue culture medium), and cultured cells (e.g., cells that are capable of extended culture in tissue culture medium). As used herein, the term "in vivo" refers to a cell that is within the body of a subject. Preferably, the cell is ex vivo.

Cells useful in the present invention have a glutamate receptor, preferably an NMDA glutamate receptor, on the cell surface. Examples of such cells include, for instance, neurons. Examples of useful neurons that can be used ex vivo include cultured neuroblastoma cells, preferably rat, mouse, or human, more preferably human. An example of a cultured human neuroblastoma cell is SHSY5Y (ATCC CRL-2266). Other examples of useful ex vivo neurons include neurons isolated from the dorsal horn of the spinal cord, dorsal root ganglia and other cell bodies of peripheral nerves, hippocampal or other limbic or cortical neurons. Preferably the neurons are removed from a rat. Examples of in vivo neurons include neurons in the spinal cord, for instance neurons in the dorsal horn and motor horn, the brain, for instance neurons in the basal forebrain and hippocampus, peripheral neurons, for instance dorsal root ganglia.

Examples of other cells useful in the present invention include, for instance, cultured synovial sarcoma cells, preferably rat, mouse, or human, more preferably human. An example of a cultured human synovial sarcoma cell is SW982 (ATCC HTB-93). Examples of in vivo cells include synovial cells lining a knee joint of a subject, preferably a human.

In an aspect of the present invention, the methods include evaluating the effect of different compounds by contacting a cell with a compound, activating a glutamate receptor, preferably an NMDA glutamate receptor, present on the cell, and detecting the distribution of the NR1 subunit in the cell. The distribution of the NR1 subunit in the cell is compared to the distribution in a cell that was not exposed to the compound. Contacting the cell with a compound can occur before, during, or after activating a glutamate receptor present in the cell. Cells ex vivo can be contacted directly with the compound by, for instance, adding the compound to the media in which the cell is bathed. Cells in vivo can be contacted directly with a compound. For instance, cells of the spinal cord can be contacted directly as described in Example 1. Alternatively, a compound can be introduced to the animal systemically as a pharmaceutical composition. Pharmaceutical compositions are detailed herein.

In another aspect of the present invention, the methods include evaluating the effect of different compounds by contacting a cell with a compound, activating a glutamate receptor, preferably an NMDA glutamate receptor, present on the cell, and detecting the production of TNFα by the cell. The amount of TNFα produced by the cell is compared to the amount of TNFα produced by a cell that was not exposed to the compound. Contacting the cell with a compound can occur before, during, or after activating a glutamate receptor present in the cell. Cells ex vivo can be contacted directly with the compound by, for instance, adding the compound to the media in which the cell is bathed. Cells in vivo can be contacted directly with a compound. Alternatively, a compound can be introduced to the animal systemically as a pharmaceutical composition.

The invention is not intended to be limited by the types of compounds that can be screened for activity using the methods described herein. Accordingly, a compound can be, for instance, a polypeptide, an organic molecule, polyketide, or a non-ribosomal peptide. Compounds useful in the methods of the present invention can be produced by natural organisms, or produced using methods known to the art including, for instance, recombinant techniques, or chemical or enzymatic synthesis techniques. Preferably, the compound is not produced by a mammal.

Preferred examples of compounds that can be used in some aspects of the present invention include tyrosine kinase inhibitors. Tyrosine kinase inhibitors are known in the art and include, for instance, Genistein (5,7-Dihydroxy-3-(4-hydroxyphenyl)-4H-1-benzopyran-4-one; 4',5,7-trihydroxy-isoflavone, Catalog Number G-103 from RBI, Natick, Mass.), Lavendustin A (5-Amino-[N-2,5-dihydroxybenzyl)-N'-2-hydroxybenzyl]salicylic acid, Catalog Number 428150 from Calbiochem, La Jolla, Calif.), and K252a (Catalog Number 420298, from Calbiochem, La Jolla, Calif.). Whether a compound is a tyrosine kinase inhibitor can be detennined using methods known in the art (see, for instance, Akiyama et al., *J. Biol. Chem.*, 262, 5592–5595 (1987) and Ohmichi et al., *Biochemistry*, 31(16:4034–4039 (1992)). Preferably, a tyrosine kinase inhibitor useful in the present invention decreases phosphorylation of NR1 receptor. Without being limiting, it is expected that a specific tyrosine kinase mediates the translocation of NR1 subunit, and that this specific tyrosine kinase will be a member of one of the known families of tyrosine kinases, for instance, the Src or Jak families. Inhibitors are available that specifically inhibit individual members of the known families of tyrosine kinases. Accordingly, it is expected that specific tyrosine kinase inhibitors will be useful in the methods of the present invention. Alternatively, it is expected that other useful compounds include tyrosine phosphatases and serine/threonine phosphatases. In other aspects of the present invention, preferred examples of compounds that can be used include tyrosine kinases, tyrosine phosphatase inhibitors, or serine/threonine phosphatase inhibitors where increases in NR1 subunit would be advantageous such as for improving memory or slowing the aging process.

The amount of a compound that is administered to alter the distribution of NR1 subunits in a cell, or alter the production of TNFα by a cell, varies depending on the type of compound used. Typically, when a compound is screened for activity in the methods of the present invention, various concentrations of the compound are used.

Activation of a neuron ex vivo can be accomplished by incubating a cell in tissue culture media and adding at least about 5 micromolar of a glutamate receptor agonist, and more preferably at least about 10 micromolar of a glutamate receptor agonist. Typically, translocation of NR1 subunit to the nuclear membrane can be observed about 4–24 hours after exposure. Neurogenic inflammatory states can be experimentally recreated ex vivo by adding at least 5 micromolar, preferably at least about 10 micromolar, of a glutamate receptor agonist to a cell that includes a glutamate receptor, and measuring the resulting production of TNFα by the cells. Alterations in the amount of TNFα produced by a cell can be observed about 4–24 hours after exposure.

Activation of a cell in vivo is typically accomplished by using an animal model that can be used for investigating conditions that result from sensitization of cells or from increased concentrations of glutamate. Without intending to be limiting, such conditions include neuropathological states and neurogenic inflammatory states. Animal models for studying these conditions are known in the art and can be used in the methods of the present invention. Models for the study of pain include those approved by the International Association for the Study of Pain. A preferred animal model for identifying compounds that alter the distribution of NR1 subunits in a cell is the rat arthritis model described in Example 1. The rat arthritis model is a commonly accepted model for the study of pain and arthritis in humans. Other animal models (for instance, using cat, monkey, or rabbit as the animal) are also commonly accepted models for these human conditions (see, e.g., Neugebauer & Schaible, *Agents and Actions*, 25, 234–236 (1988) and O'Byrne et al., *Arthritis and Rheumatism,* 33, 1023–1028 (1990)). To study pain in this model, cells in the spinal cord are exposed to a compound for a period of time, and then a knee of the animal is exposed to a stimulus that evokes persistent pain. Methods of evoking persistent pain are known in the art. After a period of time the responsiveness of the animal to an innocuous or noxious stimulus is evaluated using methods known in the art. A compound that causes an animal to have reduced primary allodynia or secondary allodynia, or reduced primary hyperplasia or secondary hyperplasia compared to an animal that has not received the compound indicates that the distribution of NR1 subunits in the spinal cord is altered. This model may also be used to study arthritis. A compound can be injected into the synovial space of a knee joint, and then the knee exposed to a stimulus that evokes arthritis. After a period of time, the responsiveness of the animal to movements in the working range of the joint are evaluated. A compound that causes an animal to have reduced response time when its foot is touched, that is, the animal overreacts, compared to an animal that has not received the compound indicates that the distribution of NR1 subunits in the cells lining the synovial space, and/or the production of TNFα by the cells is altered. Neuropathological states and neurogenic inflammatory states can also be experimentally recreated in vivo by injecting a glutamate receptor agonist into a space containing neurons (for instance, the spinal cord) or other cells (for instance, the synovial space present in a joint) that include a glutamate receptor.

The distribution of the NR1 subunits present in a cell exposed to the compound is measured and compared to a cell that has not been exposed to the compound. The distribution of NR1 subunits present in a cell can be measured using methods known in the art for determining the location of a polypeptide in a cell. For instance, the amount of NR1 subunits associated with the cellular membrane, present in the cytoplasm, or associated with the nucleus can be determined. Preferably, the amount of NR1 subunits associated with the nucleus, more preferably associated with the nuclear membrane, most preferably associated with the inner nuclear membrane is determined. The amount of NR1 subunit associated with the nucleus can be increased or decreased, preferably decreased, in a cell contacted with a compound.

Typically, the presence of NR1 is assayed using NR1-specific antibodies and methods known to the art including western immunoblot, immunoprecipitation, and immunocytochemistry. Without intending to be limiting, for example, cells can be fractionated and the different subcellular fractions tested for the presence of NR1 subunits. Alternatively, cells can be fixed and sectioned for analysis by, for instance, immunocytochemical analysis, using light microscopy or electron microscopy.

Alternatively, instead of detecting alterations in the distribution of NR1 subunits in the cell, the total amount of NR1 present in a cell contacted with a compound can be determined and compared to the total amount of NR1 present in a cell not contacted with a compound. The small amount of NR1 subunit in the nucleus normally is at the level of detection while an increase can be measured five hours after induction of knee joint inflammation. Methods for determining the total amount of a polypeptide in a cell or cell fractions are known in the art. In another alternative, instead of detecting alterations in the distribution of NR1 subunits in the cell, the amount of phosphorylated NR1 subunit present in a cell contacted with a compound can be determined and compared to the amount of the activated form of the subunit, phosphorylated NR1 present in a cell not contacted with a compound. Methods for determining whether a polypeptide is phosphorylated are known in the art.

Due to the observed presence of NR1 subunits in the nucleus, it is expected that NR1 subunits alter gene expression. Accordingly, it is expected that changes in gene expression, including alterations in transcription or translation, preferably translation, may also be used to measure alterations in the distribution of NR1 subunits in a cell.

The production of TNFα by a cell can be measured using methods known in the art, including, for instance, Enzyme-linked Immunosorbant Assay (ELISA), and ex vivo biological assays. The TNFα can be TNFα present inside the cell, secreted by the cell, or a combination thereof. Preferably, the TNFα measured is TNFα that has been secreted by the cell. Preferably, the amount of TNFα produced by a cell contacted with a compound is decreased.

The present invention is further directed to methods for treating certain conditions in a subject. The conditions include, for instance, a neuropathological state such as persistent pain, stroke, brain injury, spinal cord injury, epileptogenesis, and viral invasion, and neurogenic inflammation such as arthritis, stroke, ulcerative colitis, inflammatory bowel disease, Crohn's disease, pancreatitis, asthma, spinal cord injury, and viral invasion.

The methods include administering to the subject an effective amount of a compound that decreases or prevents a symptom of a neuropathological state or neurogenic inflammatory state. The compounds useful in this aspect of the invention are described above and can be used alone or in combination. Preferably, the compound is a tyrosine kinase inhibitor, more preferably Genistein, Lavendustin A, or K252a. The subject can be an animal, preferably a rat, a mouse, or a human, most preferably a human.

Treatment described herein can be prophylactic (initiated before a subject manifests symptoms of a condition described herein) or, alternatively, can be initiated after the development of a condition described herein. Accordingly, administration of a compound can be performed before, during, or after the occurrence of the conditions described herein. Treatment initiated after the development of a condition may result in decreasing the severity of a symptom of the condition, or completely removing a symptom of the condition. The compound can be administered systemically. When administered systemically, the compound is preferably associated with an agent that will direct the compound to the appropriate cells. For example, the compound can be associated with an antibody to a receptor present on the surface of a cell such that the compound is transported to the interior of the cell, for instance by endocytosis. Preferably, the receptor is endocytosed through clathrin-coated pits to endosomes. The compound can be administered locally. In the treatment of persistent pain that results from cancer or back pain the compound can be administered by, for instance, intraspinal catheter. In the treatment of arthritis the compound can be administered by, for instance, injection of the compound into the synovial space of the affected joint. Preferably, the compound is administered locally.

An aspect of the invention is directed to a method for treating a neuropathological state in a subject. The method includes administering to the subject an effective amount of a compound, preferably a tyrosine kinase inhibitor, more preferably Genistein, Lavendustin A, or K252a.

In some aspects of the invention, the compound used to treat the subject alters the distribution of NR1 subunit in a cell, preferably decreases the amount of NR1 subunit associated with the nucleus of a cell. Alternatively, the compound decreases the total amount of NR1 in the cell, or decreases the amount of phosphorylated NR1 in the cell. Preferably, the compound both decreases the amount of NR1 subunit associated with a cell's nucleus and decreases the total amount of NR1 in the cell. In other aspects of the invention, the compound used to treat the subject alters the production of TNFα by a cell, preferably decreases the production of TNFα by the cell. In some aspects, the compound may both alter the distribution of NR1 in a cell and alter the production of TNFα by the cell.

A neural cell can be present in the spinal cord, for instance in the dorsal horn, in the brain, for instance in the basal forebrain or hippocampus, or in the cell body of a peripheral neuron, for instance a dorsal root ganglia. Other glutamate receptor-containing cells of the present invention can be present, for instance, in the knee joint such as synovial cells. In aspects of the invention that are directed to decreasing a symptom of a neuropathological state, preferably the cell is a sensitized neuron. It is expected that decreasing a symptom of a neuropathological state results in converting a neuron from a sensitized state to a non-sensitized state. In aspects of the invention that are directed to preventing a symptom of a neuropathological state, preferably the cell is a non-sensitized neuron. It is expected that preventing a symptom of a neuropathological state results in preventing the conversion of a cell from a non-sensitized state to a sensitized state.

Also provided by the present invention are methods for treating a neurogenic inflammatory state in a subject. The method includes administering to the subject an effective amount of a compound, preferably a tyrosine kinase inhibitor, more preferably Genistein, Lavendustin A, or K252a.

In the case of a neurogenic inflammatory state of a subject caused by non-neuronal cells producing TNFα in response to a glutamate receptor agonist (for instance, arthritis, ulcerative colitis, inflammatory bowel disease, Crohn's disease, pancreatitis, asthma, stroke, brain injury, and viral invasion), it is expected that decreasing a symptom of a neurogenic inflammatory state will result in decreasing or preventing cells from producing TNFα. Without intending to be limiting, it is expected that, by reducing TNFα production, the capacity of TNFα to stimulate the inflammatory cascade is reduced, thereby decreasing, preferably preventing, a neurogenic inflammatory state.

In the case of a neurogenic inflammatory state located in the nervous system of a subject, such as neurogenic inflammation occurring during a neuropathological state of a subject (for instance, stroke, spinal cord injury, and viral invasion), TNFα expression and/or secretion from the cell is also reduced, thereby decreasing, preferably preventing, neurogenic inflammation occurring during a neuropathological state. For instance, a subject suffering from a severe spinal cord injury may develop a neuropathological state as well as a neurogenic inflammatory state. Under these circumstances, administration of a compound of the present invention is capable of decreasing, preferably preventing, the neuropathological state and the neurogenic inflammatory state.

The present invention provides methods for altering the ability of a subject to retain information, e.g., increasing the memory of a subject. The method includes administering to the subject an effective amount of a compound that increases the ability of a subject to retain information. Whether a subject is able to retain information can be determined using methods known to the art. For instance, when this method is used with non-humans, maze tests can be used, and when this method is used with humans, tests such as the California learning scale or the Wisconsin memory test can be used. Preferably, short-term memory or long-term memory is increased, more preferably, long-term memory is increased.

The compounds useful in this aspect of the invention are described above. Preferably, the compound is a tyrosine kinase, a tyrosine phosphatase inhibitor, a serine/threonine phosphatase inhibitor, or combinations thereof. Typically, the compound alters the distribution of NR1 subunit in a neuron or cells targeted by neurons, preferably by increases the amount of NR1 subunit associated with the nucleus of a neuron or cell. Alternatively, the compound increases the total amount of NR1 in the neuron or target cell, or increases the amount of phosphorylated NR1 in the neuron or target cell. Preferably, the compound both increases the amount of NR1 subunit associated with the nucleus of a neuron and increases the total amount of NR1 in the neuron. The subject can be an animal, preferably a rat, a mouse, or a human, most preferably a human. The neuron is typically present in the brain, preferably in the hippocampus.

The compound(s) useful in the methods disclosed herein is optionally and preferably present in a pharmaceutically acceptable carrier. The compounds useful in the present invention, preferably a tyrosine kinase inhibitor, may be formulated in pharmaceutical preparations in a variety of forms adapted to the chosen route of administration. Formulations include those suitable for parental administration (for instance intramuscular, intraperitoneal, intraspinal catheter, intrasynovial, or intravenous), oral, transdermal, or nasal administration. Dosages of the compositions of the invention are typically from about 0.1 mg/kg up to about 50 mg/kg intravenous or 50–250 mg/kg oral dose. Preferably, an intraspinal dose is about 10 microliters of a solution containing from about 01 micromolar to about 1 micromolar of the solution.

The formulations may be conveniently presented in unit dosage form and may be prepared by methods well known in the art of pharmacy. All methods of preparing a pharmaceutical composition include the step of bringing the active compound (e.g., a tyrosine kinase inhibitor) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

Typically, the compositions of the invention will be administered from about 1 to about 4 times per day. The amount of active ingredient that may be combined with the carrier materials to produce a single dosage form will vary depending upon the subject treated and the particular mode of administration. A typical preparation will contain from about 5% to about 95% active compound (w/w). Preferably, such preparations contain from about 20% to about 80% active compound. The amount of compound in such therapeutically useful compositions is such that the dosage level will be effective to prevent or suppress the neuropathological state or the neurogenic inflammatory state.

Formulations suitable for parenteral administration conveniently comprise a sterile aqueous preparation of the composition, or dispersions of sterile powders that include the composition, which are preferably isotonic with the blood or synovial fluid of the recipient. Isotonic agents that can be included in the liquid preparation include sugars, buffers, and sodium chloride. Solutions of the composition can be prepared in water, and optionally mixed with a nontoxic surfactant. Dispersions of the composition can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the composition, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the composition by the animal over a prolonged period can be achieved by including, for example, aluminum monostearate or gelatin.

Formulations of the present invention suitable for oral administration may be presented as discrete units such as tablets, troches, capsules, lozenges, wafers, or cachets, each containing a predetermined amount of the active compound as a powder or granules, as liposomes containing the active compound, or as a solution or suspension in an aqueous liquor or non-aqueous liquid such as a syrup, an elixir, an emulsion or a draught.

The tablets, troches, pills, capsules, and the like may also contain one or more of the following: a binder such as gum tragacanth, acacia, corn starch, or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The compound may be incorporated into sustained-release preparations and devices.

The present invention is illustrated by the following examples. It is to be understood that the particular examples, materials, amounts, and procedures are to be interpreted broadly in accordance with the scope and spirit of the invention as set forth herein.

EXAMPLE 1

Methods

Animals

All studies followed the guidelines of the Institute Animal Care and Use Committee, in accordance with the guidelines of the National Institutes of Health. All animals were hosted in a room with a constant ambient temperature of 22° C. and 12 hour light/dark cycle with free access to food and water. Eighty-five Sprague-Dawley rats (250–300 grams) total were used in experiments conducted for biochemical, behavioral, and immunocytochemistry studies. On Day 1, anesthetized animals received surgical implantation of a microdialysis fiber for spinal administration of tyrosine kinase inhibitors and inactive analogues. On Day 2 baseline behavioral testing was followed by infusion of agents for 1.5 hours (pretreatment) prior to induction of knee joint inflammation under brief anesthesia. Behavioral testing was repeated 4 hours after induction of joint inflammation. Anesthetized animals were either transcardially perfused with aldehydes for immunohistochemical studies or fresh, frozen tissues collected for biochemical studies.

Tyrosine Kinase Inhibitors

A microdialysis fiber was implanted into the spinal dorsal horn of anesthetized rats (sodium pentobarbital, 50 mg/kg) one day prior to the induction of arthritis according to the procedure of Skilling et al. (*J. Neurochem.*, 51:127–132 (1988)), as described in Sluka et al. (*Neurosci. Lett.*, 145: 141–144 (1992)). Briefly, a small midline incision was made in the skin over the T12 vertebral level. The vertebrae were cleared of muscle and two 1 millimeter (mm) holes were drilled in the lateral aspect of both sides of the T12 vertebrae to expose the L4 spinal segment. A microdialysis fiber (200 mm outer diameter, 45,000 MW cut-off, Hospal, AN69, Hospal Industrie, Meyzieu, France), was passed transversely across the deep dorsal horn and stabilized with dental cement. The microdialysis fiber was then passed through the holes in the vertebrae and transversely through the dorsal horn of the spinal cord. A 2 mm section of the microdialysis fiber lies in the dorsal horn at the level of L3–4 segment. The tubing was coated with epoxy except for a permeable portion passing through the spinal grey matter. The microdialysis fiber was connected to $PE_{20}$ tubing (Becton Dickinson and Company, San Mateo, Calif.) which was tunneled under the skin to the nape of the neck. Alternatively as a systemic control for drug administration, the microdialysis fiber was implanted only in the subcutaneous tissue over the back muscle and tunneled to the neck. Artificial cerebrospinal fluid (aCSF) was made as described by Sorkin et al. (*J. Neurosci. Methods,* 23, 131–138 (1988)) and was infused (5 microliters/minute) for 1.5 hours and then the tube was heat-sealed for use on the following day.

Two tyrosine kinase inhibitors and their inactive analogues were compared in these behavioral studies. Genistein is a protein tyrosine kinase (PTK) inhibitor that decreases NMDA currents in patch clamp studies (Wang et al., *Nature,* 369, 233–235 (1994)). Daidzein is an analogue of Genistein that lacks PTK inhibitory activity and has no effect on NMDA currents in patch clamp studies (Wang et al., *Nature,* 369, 233–235 (1994)). Lavendustin A, which is a structurally distinct PTK inhibitor that reversibly depresses NMDA currents, was also tested along with its inactive analogue, Lavendustin B. The drugs (Genistein, Lavendustin A & B and Daidzein) were dissolved in 50 percent (%) dimethyl sulfoxide (DMSO) in aCSF. Dose response curves were generated for Genistein with animals receiving Genistein spinally at concentration of 0.2 mM (n=3), 0.5 mM (n=3), 1 mM (n=9), and 2 mM (n=3). Animals received Lavendustin A or B spinally at concentrations of 0.1 mM (n=3), 0.5 mM (n=3), and 1 mM (n=5) as a positive and negative control for Genistein. The most effective dose in these pre-treatment animals was 0.5 mM. Daidzein was tested at a dose of 1 mM (n=3). The most effective dose for Genistein in these pre-treatment animals, 1 mM, was used for the systemic control animals (n=3) receiving the drug subcutaneously. Eight additional animals received the vehicle, 50% DMSO in aCSF, as a control.

Based on in vitro estimates for Genistein measured by spectrophotometer (Beckman DU®650, Beckman Coulter, Inc., Fullerton, Calif.), a maximum of about 5.6% of the drug is transferred across the microdialysis membrane measurable by high pressure liquid chromatography. Therefore, with the diffusion barriers presented by the tissue, the neurons are likely to be exposed maximally to a dose of Genistein (<56 micromolar) (µM) much lower than that inside the microdialysis fiber (1 mM). The neurons are likely to be exposed to a dose of Lavendustin (25 µM), a dose much lower than that inside the microdialysis fiber (0.5 mM).

Cycloheximide (100 milligrams per kilogram (mg/kg) intraperitoneal (i.p.) was used in some studies to determine if the alterations observed for the NMDA NR1 receptor subunit could be attributed to newly synthesized NR1 protein.

Induction of the Knee Joint Inflammation Model a. Acute Induction with Kaolin/Carrageenan.

An acute inflammatory response restricted to the knee joint can be induced by the injection of 3% kaolin and 3% carrageenan (in sterile saline; 0.1 ml; pH 7.4) into the joint cavity while the animal is briefly anesthetized with sodium methohexital (Brevital, 60 mg/kg, i.p.). Kaolin and carrageenan were obtained from Fisher Scientific, St. Louis, Mo. The knee joint is flexed manually until the rat awakes (approximately 5–10 minutes). In this arthritis model in the awake rat, localized joint swelling, as well as limping and guarding of the limb, are well developed at 4 hours (Sluka et al., *Pain*, 59, 95–100 (1994)) when behavioral testing begins.

b. Measurement of Knee Joint Circumference.

Knee joint circumference is measured in centimeters (cm) with a flexible tape measure around the center of the knee joint while the joint is held in extension as done with patients in the clinical setting as an indication of increases in joint volume. The knee joints of anesthetized rats are measured before (baseline) and four hours following injection of the knee joint with kaolin and carrageenan.

c. Comparative Measurement of Joint Temperature.

Temperature readings were documented numerically with a temperature probe after the rat is reanesthetized with sodium pentobarbital (50 mg/kg, i.p.) just prior to perfusion with aldehydes for histological preservation. Comparative temperature differences were made between the baseline temperature and the temperature four hours after induction of inflammation.

Behavioral Assessment

Fifty-five rats were used for behavioral studies. Four hours after induction of the arthritis, the joint is swollen and increased withdrawal responses to radiant heat and spontaneous guarding of the limb were noted. The increased responsiveness to noxious stimuli indicates the presence of secondary hyperalgesia. Testing of paw withdrawal latency (PWL) to radiant heat on the footpad using the Hargreaves method (Hargreaves et al., *Pain*, 32, 77–88 (1988)), as a measure of secondary hyperalgesia (away from the primary site of injury indicative of central pain) reveals that the acute inflammation renders the hindlimb more sensitive to heat stimuli (Sluka et al., *Pain*, 59, 95–100 (1994)). Briefly, animals are placed in small Lucite cubicles on a glass top table cooled with a fan and allowed to accommodate for 30 minutes prior to testing. A hand-held metal box focusing a high intensity light through an aperture (1 cm×0.8 cm) is used to apply radiant heat through the glass to the plantar surface of the hindpaw until the animal lifts its foot. Radiant heat was applied to the plantar surface of the hindpaw until the rat lifted its paw. The time which it took for this to occur was considered the PWL response time. Both paws were tested independently at five minute intervals for a total of five trials. A mean of these five reading was used as PWL response for each time point. Testing was done by the same observer for each test, and the observer was blinded to the test groups under study. A decrease in PWL occurred on the side ipsilateral to the inflamed knee 4 hours after the induction of acute arthritis and was linearly correlated with the increase in joint swelling. In the experimental rats the PWL was measured before administration of drug or vehicle (baseline) and after the drug or vehicle had been infused for 1.5 hours at which time kaolin and carrageenan was injected into the knee joint. The final measurement for PWL was at 4 hours after induction of arthritis. A decrease of the PWL to noxious radiant heat in a rat with knee joint inflammation is indicative of secondary hyperalgesia.

Immunocytochemical Localization of NMDA Receptor Subunit NR1

Twenty-four rats in 3 separate groups were used for immunocytochemical studies. One group of rat (n=8) was a naive control. The other 2 groups (n=16) of rats received surgical placement of the microdialysis fiber placement. On the day after microdialysis fiber placement, the animals were treated spinally with either Genistein (1 mM) or vehicle (50% DMSO in aCSF) for 1.5 hours (n=8 for each group). Then the left knee joint of all sixteen rats was injected with 0.1 ml of kaolin and carrageenan.

Animals were anesthetized and transcardially perfused with a brief warm saline rinse followed by fixative solution (4% paraformaldehyde in 0.1 M phosphate buffer, pH 7.4). The tissues were soaked overnight in 30% buffered sucrose and cut at 30 microns on a sliding microtome. For light microscopy, the tissues from animals (n=8) were permeabilized with a 50% buffered ethanol treatment. Tissue sections were then stained immunocytochemically for glutamate receptor subunit NR1 and phospho-NR1. Primary antibodies to be used for staining include anti-NMDA NR1 NMDA receptor (0.5–1 milligrams per milliliter (mg/ml)) purchased from ChemIcon Inc. (Pittsburgh, Pa.). Other neurotransmitter and receptor primary antibodies against NMDA NR2C, mGluR1, and mGluR5 were used as stain specificity controls. The primary antibodies were diluted in phosphate buffered saline (PBS, pH 7.6) with 0.1% BSA for overnight incubation on the spinal cord tissues. After washing in PBS, the tissue sections were incubated in the appropriate secondary antibody, either anti-mouse or anti-rabbit IgG (1:100, 30 minutes) and in avidin-biotin complex (ABC, 1:100, Vector Laboratories, Burlingame, Calif.). Sections were reacted with diaminobenzidine (DAB) solution (1.5 mg/ml) as the chromogen and peroxide (0.5 mg/ml) to produce a dense reaction product. To further intensify the reaction product particularly for visualization of nuclear rings, some tissues were reacted with colloidal gold conjugated IgG and reacted with a silver chloride solution to produce an intense black reaction product (Takizawa et al., *J. Histochemistry & Cytochemistry*, 42, 1615–1623 (1994)).

Immunocytochemical controls included sections processed in the absence of the primary or secondary antibody or ABC reagents. The specificity of the transmitter antibodies was confirmed by appearance of a single band by Western blot. In addition to use of the C-terminus NR1 antibody from ChemIcon, an antibody directed to the N-terminus of the NR1 protein was used as control (1 mg/ml; BD PharMingen, San Diego, Calif.).

For electron microscopy, the animals (n=3) were perfused with a mixture of 2.5% glutaraldehyde and 1% paraformaldehyde. The lumbar cords were cut at a 30 mm thickness with a vibratome. After pretreatment with 1% sodium borohydride and the 50% buffered ethanol, tissue sections were processed for immunocytochemical staining for mGluR1 and mGluR2/3 as above. Tissues were dehydrated in alcohols, embedded in plastic resin, hardened and thin sectioned for electron microscopy.

Results

Behavioral Studies

Reflexive withdrawal of the paw (PWL) to radiant heat is known to be reduced from baseline 4 hours after induction of knee joint inflammation in this arthritis model in rats (Sluka et al., *Neurosci. Lett.*, 145:141–144 (1992)). Comparisons were made with baseline and between treatment groups at 4 hours after joint inflammation (ANOVA). The behavioral studies demonstrated that pre-treatment with the protein tyrosine kinase inhibitor, Genistein, significantly attenuates the inflammation-induced decrease in PWL in response to radiant heat indicative of secondary hyperalgesia and a central sensitization state in the central nervous system in this arthritis model. Secondary hyperalgesia requires sensitization of various portions of the neuronal circuitry in addition to the local spinal reflex loop. Secondary hyperalgesia which can be measured is a manifestation of central sensitization. Thus central sensitization is sensitization of structures of the pain circuitry as opposed to sensitization of the peripheral nerve of the spinal loop.

As shown in FIG. 1, Genistein and Lavendustin A significantly (p<0.05 versus 4 hours vehicle group) attenuated the PWL decreases induced by knee joint inflammation in all treatment groups. Genistein (1 mM) and other agents tested did not affect baseline PWL. The structurally distinct PTK inhibitor, Lavendustin A, also significantly abrogated the development of secondary hyperalgesia. While the secondary hyperalgesia did not develop when Genistein and Lavendustin A were administered, other inflammatory signs were evident including the expected increases in joint circumference and temperature.

Secondary hyperalgesia typical of this model developed after administration of vehicle and the inactive analogues, Daidzein and Lavendustin B. Thus, control treatment with inactive analogs, Lavendustin B and Daidzein, were ineffective in altering the nociceptive outcome of knee joint inflammation. Secondary hyperalgesia is a centrally mediated form of nociceptive sensitization typical of the kaolin/carrageenan knee joint and other pain models. Since the tyrosine kinase inhibitor was applied directly to the affected spinal cord segment by microdialysis, this confirms the requirement of tyrosine phosphorylation in long-term plastic changes occurring in the spinal cord that result in the development of secondary hyperalgesia. While ongoing peripheral increases in joint temperature and circumference were unaffected by this treatment, the nociceptive changes are not present after inhibition of protein tyrosine kinase.

Immunocytochemical Localization of Glutamate NMDA Receptor Subunit NR1

Figure 2:
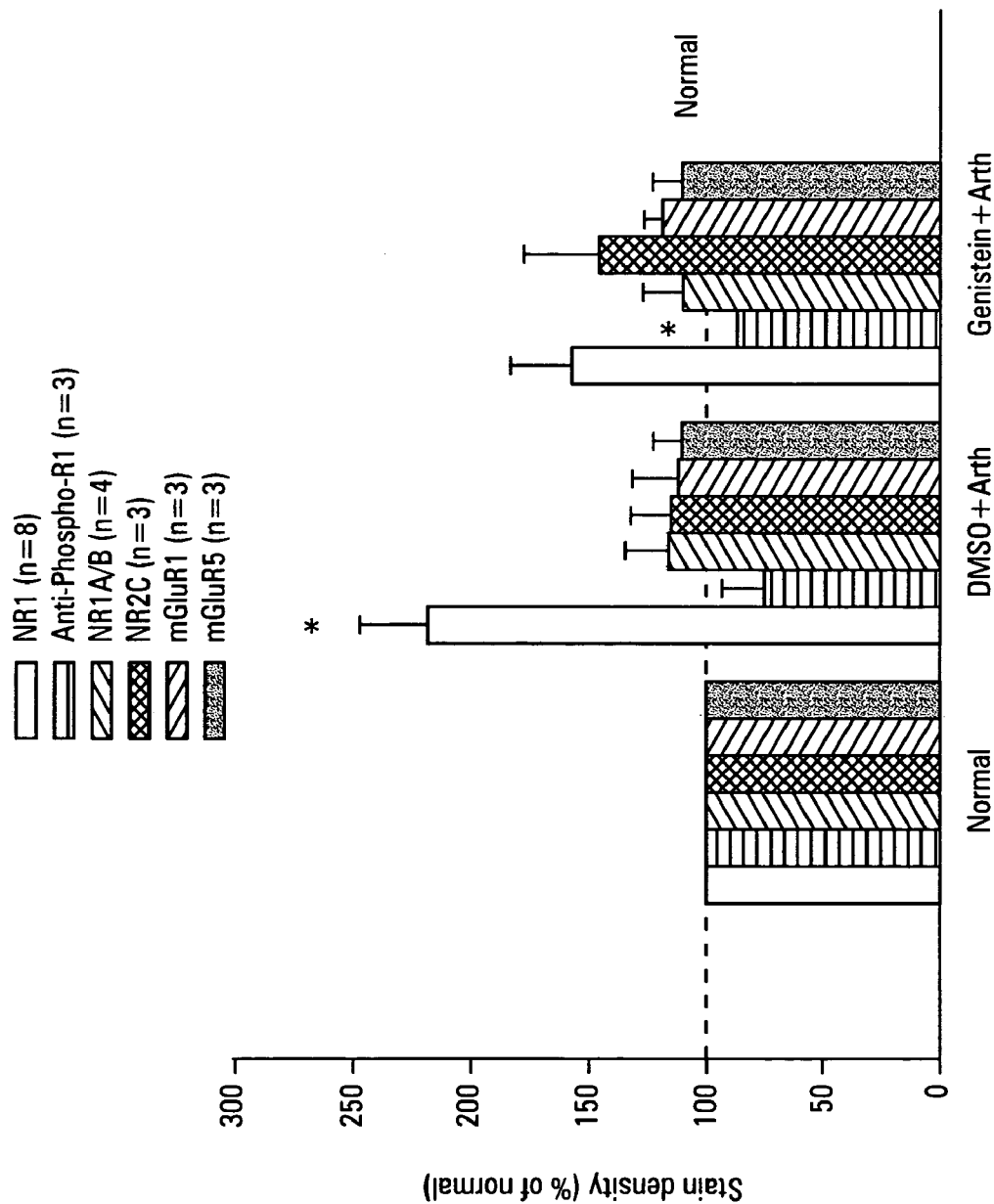
FIG. 2. The effect of Genistein pre-treatment on NR1 stain density in the superficial dorsal horn (I–II) of the spinal cord in rats. Normal, density of receptors in the superficial dorsal horn (I–II) of the spinal cord in rats not treated; vehicle (dimethyl sulfoxide, DMSO)+Arthritis density of receptors in the superficial dorsal horn (I–II) of the spinal cord in rats treated with DMSO 1.5 hours before treatment of the knee joint with the irritant kaolin/carrageenan; Genistein+Arthritis, density of receptors in the superficial dorsal horn (I–II) of the spinal cord in rats treated with the tyrosine kinase inhibitor, Genistein 1.5 hours before treatment with kaolin/carrageenan; *, t-test for independent samples, $p<0.05$ (versus normal); NR1, NMDA glutamate receptor NR1 subunit; phospho-R1, antibody for phosphatase activated NMDA glutamate receptor NR1 subunit; NR1 A/B, NMDA glutamate receptor NR1 subunit subtypes A/B; NR2C, NMDA glutamate receptor NR2 subunit subtype C; mGluR1, group 1 metabotropic glutamate receptor; mGluR5, Group 5 metabotropic glutamate receptor; n, number of animals.

The density of immunocytochemical staining for NMDA NR1 in the lumbar enlargement on the side of the inflamed knee joint at 4 hours was greatly increased after induction of knee joint inflammation. The increases were evident as a diffuse stain density increase throughout the spinal grey matter. Computer-assisted measurement of immunocytochemical staining at the site of greatest increase in lamina I and II indicated that stain density for NR1 was doubled in normal controls (FIG. 2). This increase was significant ($P<0.05$). Other NMDA receptor subunits tested, including NR2A/B, NR2C, mGluR1, and mGluR5 did not increase after knee joint inflammation. Likewise, an antibody to the phosphorylated form of NR1 did not increase after induction of knee joint inflammation. In fact, at 4 hours after induction of the arthritis model, the staining density for the phosphorylated form of NR1 was significantly decreased compared to normal control animals. The rapid increase in NR1 staining also included a shift in the localization pattern within the cell.

Figure 3:
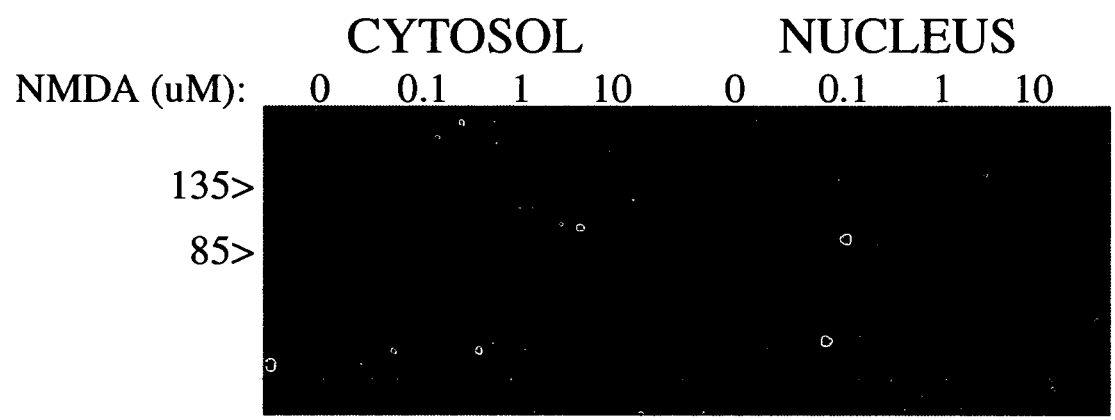
FIG. 3. Western blot analysis detecting the presence of the glutamate NR1 receptor subunit in cytosolic and nuclear extracts from cultured clonal human synovial cells SW982 treated with increasing concentrations of NMDA.

Significant quantities of NMDA NR1 were localized along the nuclear membrane in animals with inflamed knee joints, forming a ring pattern at light level (FIG. 2). With electron microscopy it was evident that the localization of NMDA NR1 was located on the inner nuclear membrane especially at nuclear pore sites where post-transcriptional modifications can occur (FIG. 3).

After pre-treatment with Genistein, staining for NR1 was about half that observed in arthritic rats and was not significantly increased above levels seen in normal rats (FIG. 2). Likewise, the nuclear localization was greatly reduced. Staining was identical with specific antibodies directed against either the C- or N-terminus of the NR1 receptor subunit. Pre-treatment with cycloheximide to eliminate de novo synthesis reduced the increase in NR1 staining by about half.

After induction of inflammation, the NMDA receptor subunit, NR1, is the only NMDA receptor subunit tested that increased. The increased expression of NR1 occurred throughout the grey matter of the spinal cord on the same side as the knee joint inflammation. Genistein treated arthritic animals had greatly reduced expression increases for NR1 that were not significantly different from baseline. Genistein also inhibited the shift in the pattern of NMDA NR1 protein staining from a light diffuse staining previously shown with electron microscopy to represent post-synaptic membrane localization (Liu et al., *Proc. Natl. Acad. Sci.*, 91:8383–8387 (1994)) to that evident as nuclear translocation to the inner nuclear membrane shown here with electron microscopy. The localization forms a ring pattern at the nuclear membrane notable at light level within 4 hours after induction of arthritis. Thus, the nuclear translocation event is mediated by protein tyrosine kinase phosphorylation. Since cycloheximide reduced these increases it is likely that some of the increases in NR1 including the nuclear localization, represent newly synthesized NR1. Cycloheximide, which prevents protein synthesis, did not totally reduce the staining to baseline suggesting that some of the NR1 is translocating to the nucleus as well (see also results of Western blot analysis below).

The Role of NMDA Receptor NR1 Subunit Nuclear Translocation

The nuclear translocation of NMDA NR1 at nuclear pore sites suggests the ability of the NMDA NR1 subunit to function at the nuclear membrane in nuclear trafficking or perhaps to assist in other calcium-mediated events if dimers are formed. This signal transduction event requires tyrosine kinase phosphorylation. These results indicate that the NR1 subunit is involved in glutamate mediated intracellular signaling pathways leading to central sensitization after nociceptive activation.

EXAMPLE 2

This example demonstrates that the translocation of NR1 subunit that was observed in animals also occurs in cultured cell lines.

Ex Vivo Studies

The cultured cell lines used in these studies were the human neuroblastoma clonal line, SHSY5Y, and the human synovial sarcoma clonal line, SW982, both available through the American Tissue Type Culture Collection (item number CRL 2266 and HTB-93, respectively). Cells were grown in Dulbecco's Modification of Eagles Medium (DMEM) without L-glutamine, with 4.5 grams/Liter glucose, and with 10% bovine fetal serum in a tissue culture incubator at 37° C. in a gaseous mixture of $O_2/CO_2$. Cells were routinely split as necessary to maintain proper cell density. Cells were removed from plates by adding TRYPSIN/EDTA in Hank's Balanced Salt solution. After cell counts, approximately 10,000 cells were plated per well in a culture dish. For experiments, the cells were plated into 35 mm Petri dishes or 6- or 24-well plates as needed.

Cell Culture Treatments

For immunocytochemistry experiments and some western blot experiments, SW982 cells were exposed to glutamate (1 µM to 10 µM), or glutamate analog NMDA (or related glutamate compound)(5 µM) and Genistein (10 mM). At various timepoints of exposure, including 4, 12, and 24 hours, cells were collected for Western blot measurement of NR1 or fixed with aldehydes and stained to visualize the location of glutamate receptor subunit NR1 using a specific antibody directed to either the C-terminus or the N-terminus of the NR1 protein.

For detection of released Tumor Necrosis Factor alpha (TNFα) and some western blot experiments, cells were exposed to the two glutamate agonists NMDA (5 mM) and ACPD (5 mM), in the presence or absence of the tyrosine kinase inhibitors Genistein (10 mM) or K252a (100 nM). After 24 hours the culture medium was collected and processed for TNFα detection (see below) while the cells were lysed into cytosolic and nuclear protein fractions and processed for western blot analysis as described also below.

Immunocytochemistry

Immunohistochemistry was used to identify glutamate receptor subtypes present on cultured synoviocytes and neuroblastoma cells. Cells are treated with fixative solution (4% paraformaldehyde in 0.1 M phosphate buffer, pH 7.4) for 1 hour. Cultures are rinsed thoroughly (6 times) with phosphate buffered saline (PBS) with 0.1% BSA. Primary antibodies used for staining include anti-NMDA NR1 glutamate receptor purchased from Chemicon (Temecula, Calif. Catalog Number AB1516) (0.5–1 mg/ml) which will bind with the C-terminus of the ionotropic NMDA glutamate receptor NR1 subunit specifically and the anti-NMDA NR1 antibody from Pharmingen (San Diego, Calif. Catalog Number 60021A) (1 mg/ml) which binds to the N-terminus of the NMDA glutamate receptor NR1 subunit specifically. Other neurotransmitter and receptor primary antibodies are also available in the lab for use as positive controls including antibodies for the metabotropic glutamate receptors (anti-mGluR1 Catalog Number 06-310, and anti-mGluR5 Catalog Number 06-451 from Upstate Biotechnology located in Lake Placid, N.Y.) and are used in dilutions of 1:1,000–1:10,000 (adjusted empirically). The primary antibodies were diluted in phosphate buffered saline (PBS) with 0.1% BSA for overnight incubation on the spinal cord tissues. After washing in PBS (pH 7.6) the tissue sections were incubated in the secondary antibody, goat anti-rabbit IgG with a fluorescent ALEXA tag (1:100, 30 minutes) (Molecular Probes, Eugene, Oreg., Catalog Number A-11012). Immunocytochemical controls included sections processed in the absence of the primary or secondary antibody. The specificity of the transmitter antibodies were confirmed by adsorption controls with excess antigen. Specific binding with antibodies identifying both the C- and the N-terminus, one of which was a monoclonal antibody, confirmed the identity of the NR1 protein localization in the nucleus.

Western Blot Analysis

Western blot analysis was used to measure NR1 in both nuclear and cytosolic or total protein extracts using established methods (Kaufmann et al., *J. Neurochem.*, 76, 1099–1108 (2001)). Extractions (20 μg of protein from nuclear/cytosolic fractions or 20–40 μg of protein from total cell fractions) were diluted in 4× SDS loading buffer (each 100 ml of buffer contains: 3 grams (g) Tris; 8 g SDS; 2.5 g DTT; 0.05 g Bromophenol blue; 40% [v:v] glycerol) and loaded onto a 10% SDS-polyacrylamide denaturing gel. After electrophoresis (1–2 hours at 50 milliamps (mA)), the gel was blotted onto nitrocellulose membrane by overnight electrophoretic transfer. After blocking for 30 minutes at room temperature with Tris-buffered saline containing 5% milk, membranes were then incubated with a human NR1 rabbit polyclonal antibody (dilution 1:1,000 v:v, Chemicon, Temecula, Calif., Catalog Number AB1516) in Tris-buffered saline containing 2.5% powdered milk for 1 hour at room temperature. Membranes were washed twice with Tris-buffered saline and then for 1 hour at room temperature in Tris-buffered saline containing 2.5% powdered milk with an HRP-conjugated goat anti-rabbit antibody (dilution 1:7,500 v:v, Biorad, Hercules, Calif., Catalog Number 170/6515). After three washes with Tris-buffered saline, immunoreactive bands were detected by a chemiluminescent Western blot detection kit (Amersham, Buckinghamshire, UK, Catalog Number RPN2106) according to the manufacturer's instructions.

Enzyme-linked Immunosorbant Assay (ELISA)

The release of the inflammatory mediator and initiator of inflammatory cascades, TNFα was measured by ELISA using a commercially available kit (R&D Quantikine, Catalog Number DTA50) specific for human TNFα. The SW982 cell culture media was removed as described above and centrifuged at 800× g for 10 minutes to remove floating cells and debris. The supernatant was then used to measure released TNFα using the R&D ELISA kit (DTA 50, Berkeley, Calif.) according to the manufacturer's instructions.

Results

Immunocytochemistry for clonal lines in culture treated with NMDA or NMDA plus a metabotropic glutamate receptor agonist replicated the visualization of NR translocation to the nucleus. This was observed for both the neuroblastoma and synovial clonal cell models, indicating that this is a general phenomenon of all cells and is not limited to the nervous system.

Western blot analysis allowed measurement of NR1 subunit either as a total, nuclear, or cytosolic content. FIG. 3 shows results from experiments where it was determined by western blot analysis the presence of the NR1 subunit in purified cytosolic and nuclear extracts from cultured human clonal synovial cells treated for 12 hours with increasing concentrations of NMDA. A dose-dependent reduction of NR1 in the cytosol was accompanied by the appearance of NR1 in the nuclear compartment, thus suggesting that stimulation of glutamate receptors in synovial cells promotes NR1 nuclear translocation.

Figure 4:
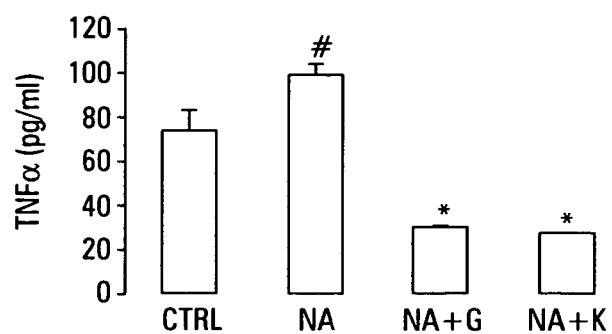
FIG. 4. Tumor necrosis factor-alpha (TNF-α) levels in the culture medium of clonal human synovial cells SW982 treated with NMDA and (1S, 3R)-1-aminocyclopentane-1, 3-dicarboxylic acid ACPD (N+A) in the presence of the tyrosine kinase inhibitors Genistein (G) or K252a (K). N=3 independent replicas per group. # and *: $p<0.01$ vs. control or NA-treated cells, respectively (unpaired Student's "t" test), pg/ml, picograms per milliliter.

These data indicate that activation of glutamate receptors results in a neurogenic induction of TNFα release from synovial cells, the TNFα release is blocked by tyrosine kinase inhibitors. FIG. 4 shows the results of an experiment where the levels of TNFα were determined in the culture medium of SW982 human synovial cells treated with NMDA and ACPD in the presence of two tyrosine kinase inhibitors, Genistein and K252a. The NMDA glutamate and metabotropic glutamate receptor agonist, ACPD, treatment significantly promoted release of TNFα from the cultured synoviocytes. As predicted, NMDA/ACPD-promoted release of TNFα was completely abolished by either Genistein or the more specific tyrosine kinase inhibitor, K252a. These findings suggest that the activation of glutamate receptors, possibly involving the nuclear translocation of receptor subunit NR1, is an important event leading to, for example, activation of inflammatory cascades by causing the release of TNFα from synovial lining cells in culture and may also occur, as in the case of arthritic knee joint.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for altering NR1 subunit distribution in a test cell by decreasing the amount of NR1 subunit associated with a nucleus of the test cell, the method comprising:

contacting a test cell with a tyrosine kinase inhibitor, activating an NMDA glutamate receptor present on the test cell and on a control cell not contacted with a tyrosine kinase inhibitor; and detecting the distribution of NR1 subunit associated with the nucleus in the test cell and the control cell, wherein a decrease in the amount of NR1 subunit associated with the nucleus of the test cell relative to the control cell indicates the alteration of NR1 subunit distribution.

2. A method for altering NR1 subunit distribution in a test cell by increasing the amount of NR1 subunit associated with a nucleus of the test cell, the method comprising:

contacting the test cell with a tyrosine phosphatase inhibitor, activating an NMDA glutamate receptor present on the test cell and on a control cell not contacted with the tyrosine kinase inhibitor; and detecting the distribution of NR1 subunit associated with the nucleus in the test cell and the control cell, wherein an increase in the amount of NR1 subunit associated with the nucleus of the test cell relative to the control cell indicates the alteration of NR1 subunit distribution.

3. A method for identifying a compound that alters NR1 subunit distribution in a test cell by decreasing the amount of NR1 subunit associated with a nucleus of the test cell, the method comprising:

contacting the test cell with a compound;

activating an NMDA glutamate receptor present on the test cell and on a control cell not contacted with the compound; and detecting an alternation in the distribution of NR1 subunit in the test cell, wherein a decrease in the amount of NR1 subunit associated with a nucleus of the test cell relative to the control cell indicates the compound alters NR1 subunit distribution in the test cell.

4. A method for identifying a compound that alters NR1 subunit distribution in a test cell by increasing the amount of NR1 subunit associated with a nucleus of the test cell, the method comprising:

contacting the test cell with a compound;

activating an NMDA glutamate receptor present on the test cell and on a control cell not contacted with the compound; and detecting an alteration in the distribution of NR1 subunit in the test cell, wherein an increase in the amount of NR1 subunit associated with a nucleus of the test cell relative to the control cell indicates the compound alters NR1 subunit distribution in the test cell.

5. A method for identifying a compound that alters the amount of NR1 subunit distribution in a test cell by decreasing the amount of NR1 subunit associated with a nucleus of the test cell and decreasing the total amount of NR1 subunit in the cell, the method comprising:

contacting the test cell with a compound;

activating an NMDA glutamate receptor present on the test cell and on a control cell not contacted with the compound; and detecting a decrease in the amount of NR1 subunit associated with a nucleus of the test cell relative to the control cell and;

detecting a decrease in the total amount of NR1 subunit in the test cell relative to the control cell, wherein detecting a decrease in the amount of NR1 subunit associated with the nucleus of the test cell relative to the control cell and a decrease in the total amount of NR1 in the test cell relative to the control cell indicates that the compound alters the amount of NR1 subunit associated with a nucleus of the test cell and the total amount of NR1 in the test cell.

6. A method for identifying a compound that alters the amount of NR1 subunit distribution in a test cell by increasing the amount of NR1 subunit associated with a nucleus of the test cell and increasing the total amount of NR1 subunit in the cell, the method comprising:

contacting the test cell with a compound;

activating an NMDA glutamate receptor present on the test cell and on a control cell not contacted with the compound; and detecting an increase in the amount of NR1 subunit associated with a nucleus of the test cell relative to the control cell and detecting an increase in the total amount NR1 subunit in the test cell relative to the control cell, wherein the detecting an increase in the amount of NR1 subunit associated with the nucleus of the test cell relative to the control cell and an increase in the total amount of NR1 in the test cell relative to the control cell indicates that the compound alters the amount of NR1 subunit associated with a nucleus of the test cell and the total amount of NR1 in the test cell.

7. A method for identifying a tyrosine kinase inhibitor that alters NR1 subunit distribution in a test cell by decreasing the amount of NR1 subunit associated with a nucleus of the test cell, the method comprising:

contacting the test cell with a tyrosine kinase inhibitor;

activating an NMDA glutamate receptor present on the test cell and on a control cell not contact with the tyrosine kinase inhibitor; and detecting an alteration in the distribution of NR1 subunit in the test cell, wherein detecting a decrease in the amount of NR1 subunit associated with a nucleus of the test cell relative to the control cell indicates the tyrosine kinase inhibitor alters NR1 subunit distribution in the test cell.

8. A method for identifying a tyrosine phosphatase inhibitor that alters NR1 subunit distribution in a test cell by increasing the amount of NR1 subunit associated with a nucleus of the test cell, the method comprising:

contacting the test cell with a tyrosine phosphatase inhibitor;

activating an NMDA glutamate receptor present on the test cell and on a control cell not contacted with the tyrosine kinase inhibitor; and detecting an alteration in the distribution of NR1 subunit in the test cell; wherein detecting an increase in the amount of NR1 subunit associated with a nucleus of the test cell relative to the control cell indicates the tyrosine kinase inhibitor alters NR1 subunit distribution in the test cell.

9. The method of claim 3, wherein the cell is a neuron.

10. The method of claim 3, wherein the contacting a cell with a compound occurs before, during, or after activating an NMDA glutamate receptor present on the cell.

11. The method of claim 3, wherein the compound is selected from the group consisting of a tyrosine kinase inhibitor, a tyrosine phosphatase, and a serine/threonine phosphatase.

12. The method of claim 3, wherein the compound is selected from the group consisting of a tyrosine kinase, a tyrosine phosphatase inhibitor, and a serine/threonine phosphatase inhibitor.

13. The method of claim 4, wherein the cell is a neuron.

14. The method of claim 4, wherein the contacting a cell with a compound occurs before, during, or after activating an NMDA glutamate receptor present on the cell.

15. The method of claim 4, wherein the compound is selected from the group consisting of a tyrosine kinase inhibitor, a tyrosine phosphatase, and a serine/threonine phosphatase.

16. The method of claim 4, wherein the compound is selected from the group consisting of a tyrosine kinase, a tyrosine phosphatase inhibitor, and a serine/threonine phosphatase inhibitor.

17. The method of claim 5, wherein the cell is a neuron.

18. The method of claim 5, wherein the contacting a cell with a compound occurs before, during, or after activating an NMDA glutamate receptor present on the cell.

19. The method of claim 5, wherein the compound is selected from the group consisting of a tyrosine kinase inhibitor, a tyrosine phosphatase, and a serine/threonine phosphatase.

20. The method of claim 5, wherein the compound is selected from the group consisting of a tyrosine kinase, a tyrosine phosphatase inhibitor, and a serine/threonine phosphatase inhibitor.

21. The method of claim 6, wherein the cell is a neuron.

22. The method of claim 6, wherein the contacting a cell with a compound occurs before, during, or after activating an NMDA glutamate receptor present on the cell.

23. The method of claim 6, wherein the compound is selected from the group consisting of a tyrosine kinase inhibitor, a tyrosine phosphatase, and a serine/threonine phosphatase.

24. The method of claim 6, wherein the compound is selected from the group consisting of a tyrosine kinase, a tyrosine phosphatase inhibitor, and a serine/threonine phosphatase inhibitor.

25. The method of claim 7, wherein the cell is a neuron.

26. The method of claim 7, wherein the contacting a cell with a compound occurs before, during, or after activating an NMDA glutamate receptor present on the cell.

27. The method of claim 8, wherein the test cell and the control cell is neuron.

28. The method of claim 8, wherein the contacting a cell with a compound occurs before, during, or after activating an NMDA glutamate receptor present in the cell.

* * * * *